United States Patent
Samadani et al.

(10) Patent No.: US 9,662,023 B2
(45) Date of Patent: May 30, 2017

(54) ROBUST HEART RATE ESTIMATION

(71) Applicant: QUALCOMM Incorporated, San Diego, CA (US)

(72) Inventors: Ramin Samadani, Menlo Park, CA (US); Carlos Manuel Puig, Santa Clara, CA (US); Russel Allyn Martin, Menlo Park, CA (US); Victor Kulik, San Jose, CA (US)

(73) Assignee: QUALCOMM Incorporated, San Diego, CA (US)

( * ) Notice: Subject to any disclaimer, the term of this patent is extended or adjusted under 35 U.S.C. 154(b) by 189 days.

(21) Appl. No.: 14/741,425

(22) Filed: Jun. 16, 2015

(65) Prior Publication Data

US 2016/0367158 A1 Dec. 22, 2016

(51) Int. Cl.
*A61B 5/024* (2006.01)
*A61B 5/00* (2006.01)

(52) U.S. Cl.
CPC ...... *A61B 5/02427* (2013.01); *A61B 5/02416* (2013.01); *A61B 5/02438* (2013.01); *A61B 5/721* (2013.01); *A61B 5/7221* (2013.01); *A61B 5/7278* (2013.01)

(58) Field of Classification Search
CPC .. A61B 5/02438; A61B 5/721; A61B 5/02416
See application file for complete search history.

(56) References Cited

U.S. PATENT DOCUMENTS 8,888,700 B2 11/2014 Banet et al.
8,934,952 B2 1/2015 Leboeuf et al.
2002/0151775 A1 10/2002 Kondo
2005/0075553 A1 4/2005 Sakai et al.
2011/0125063 A1 5/2011 Shalon et al.
2014/0018635 A1 1/2014 Buchheim et al.
(Continued)

FOREIGN PATENT DOCUMENTS

JP 2001078973 A 3/2001

OTHER PUBLICATIONS

International Search Report and Written Opinion—PCT/US2016/032711—ISA/EPO—Jul. 18, 2016.
(Continued)

*Primary Examiner* — Michael Kahelin
(74) *Attorney, Agent, or Firm* — Silicon Valley Patent Group LLP

(57) ABSTRACT

Disclosed embodiments pertain to the measurement of heart rate in the presence of motion and noise. Spectral peaks in measurements by an optical sensor are compared with spectral peaks obtained from a motion sensor signal measurements, to obtain a fundamental frequency in the optical sensor signal, where the fundamental frequency is associated with a user's heart rate. A first heart rate may be estimated based on the fundamental frequency. A variety of quality metrics may be determined for the first heart rate estimate. A second estimated heart rate may be determined based by processing a frequency domain representation of the optical sensor signal based on a frequency domain representation of the motion sensor signal. One or more of the previously determined quality metrics may be dynamically adjusted based on a comparison of first and second estimated heart rates.

30 Claims, 9 Drawing Sheets

(56) References Cited

U.S. PATENT DOCUMENTS

2014/0100434 A1    4/2014  Diab et al.
2014/0213858 A1*   7/2014  Presura ................. A61B 5/721
                                                          600/301
2014/0275852 A1    9/2014  Hong et al.

OTHER PUBLICATIONS

Patterson J., et al., "Ratiometric Artifact Reduction in Low Power Reflective Photoplethysmography", IEEE Transactions on Biomedical Circuits and Systems, XP011336431, Aug. 2011, vol. 5, No. 4, pp. 330-338.

Allen, J., "Photoplethysmography and its application in clinical physiological measurement," Physiological Measurement 28(3), Feb. 20, 2007, pp. R1-R39.

Asada H. H., et al., "Active Noise Cancellation using MEMS Accelerometers for Motion-Tolerant Wearable Bio-sensors", Proceedings of the 26th Annual International Conference of the IEEE EMBS, Sep. 1-5, 2004, vol. 3, pp. 2157-2160.

\* cited by examiner

340

```
           ┌─────┐
           │ 340 │
           └──┬──┘
              ▼
```

342
Obtain First Quality Metric Factor as the Ratio of:
   (i)    Sum of Amplitude of Fundamental Frequency and the Amplitude of Optical Sensor Peaks that are Integral Multiples of the Fundamental Frequency;
to
   (ii) Sum of Amplitudes of All Spectral Peaks

344
Obtain Second Quality Metric as Ratio of:
  (i) Power of Fundamental Spectral Peak and
  (ii) Power at Designated Distance from Fundamental Spectral Peak

346
Optionally Obtain Third Quality Metric by combining First & Second Quality Metrics

ROBUST HEART RATE ESTIMATION

FIELD

This disclosure relates generally to apparatus, systems, and methods for biometric measurements including cardiovascular measurements such as heart rate.

BACKGROUND

Modern mobile devices may include sensors such as optical sensors, which are used to measure biometric information. For example, a photoplethysmogram (PPG) sensor obtains volumetric measurements of blood vessels near the skin surface. When the heart pumps blood, the resulting pressure pulse causes changes to blood vessels. The pressure pulse may distend arteries and arterioles in skin tissue. An optical sensor, such as a PPG sensor, may be used to detect a change in blood vessel volume caused by the pressure pulse. Blood vessel volume change caused by the pressure pulse is detected by illuminating the skin with the light from a light-emitting diode (LED) and then measuring the amount of light either transmitted or reflected to a photodiode. Blood vessel volume change caused by blood flow to the skin may be modulated by various physiological parameters. Therefore, the information provided by PPG sensors may be used to obtain a variety of biometric measurements.

One drawback of optical sensors, such as PPG sensors, is that the biometric measurements obtained are sensitive to user movement. Thus, even small user movements such as typing, hand movement, and/or other subtle movements can affect the measurements and introduce noise and other artifacts into the measured signals.

SUMMARY

According to some aspects, a processor-implemented method may comprise: obtaining a plurality of optical sensor signal measurements of an optical sensor signal, the optical sensor signal measurements based, in part, on at least one cardiovascular parameter of a user; and obtaining a plurality of motion sensor signal measurements of a motion sensor signal, the motion sensor signal measurements based, in part, on motion of the user. The method may further comprise: determining, based, in part, on a comparison of a spectral peaks obtained from the optical sensor signal measurements and spectral peaks obtained from the motion sensor signal measurements, a fundamental frequency associated with the optical sensor signal. A first heart rate may be estimated based, in part, on the fundamental frequency. In some embodiments, the method may further comprise obtaining a first quality metric associated with the first heart rate. The first quality metric may be based, at least in part, on: a first sum, wherein the first sum is obtained by adding an amplitude of a spectral peak corresponding to the fundamental frequency to amplitudes of spectral peaks in a first subset of spectral peaks in the optical sensor signal, wherein the first subset of spectral peaks is selected from spectral peaks associated with integral multiples of the fundamental frequency in the optical sensor signal, and a second sum obtained by adding the amplitudes of spectral peaks in a second subset of spectral peaks in the optical sensor signal, wherein the second subset of spectral peaks is selected from a set of spectral peaks in the optical sensor signal.

In another aspect a mobile device may comprise: an optical sensor to provide a plurality of optical sensor signal measurements of an optical sensor signal based, in part, on at least one cardiovascular parameter of a user; a motion sensor to provide a plurality of motion sensor signal measurements of a motion sensor signal based, in part, on motion of the user; and a processor coupled to the optical sensor and the motion sensor. In some embodiments, the processor may be configured to: determine, based, in part, on a comparison of spectral peaks obtained from the optical sensor signal measurements and spectral peaks obtained from the motion sensor signal measurements, a fundamental frequency associated with the optical sensor signal. The processor may be further configured to: estimate a first heart rate based, in part, on the fundamental frequency; and obtain a first quality metric associated with the first heart rate. In some embodiments, the first quality metric may be based, at least in part, on: a first sum, wherein the first sum is obtained by adding an amplitude of a spectral peak corresponding to the fundamental frequency to amplitudes of spectral peaks in a first subset of spectral peaks in the optical sensor signal, wherein the first subset of spectral peaks is selected from spectral peaks associated with integral multiples of the fundamental frequency in the optical sensor signal, and a second sum obtained by adding the amplitudes of spectral peaks in a second subset of spectral peaks in the optical sensor signal, wherein the second subset of spectral peaks is selected from a set of spectral peaks in the optical sensor signal.

In a further aspect, an apparatus may comprise: optical sensing means to provide a plurality of optical sensing means signal measurements of an optical sensing means signal based, in part, on at least one cardiovascular parameter of a user; motion sensing means to provide a plurality of motion sensing means signal measurements of a motion sensing means signal based, in part, on motion of the user; and processing means coupled to the optical sensing means and the motion sensing means. In some embodiments, the processing means may comprise: means for determining, based, in part, on a comparison of a spectral peaks obtained from the optical sensing means signal measurements and spectral peaks obtained from the motion sensing means signal measurements, a fundamental frequency associated with the optical sensing means signal. In some embodiments, the processing means may further comprise: means for estimating a first heart rate based, in part, on the fundamental frequency; and means for obtaining a first quality metric associated with the first heart rate. In some embodiments, the first quality metric may be based, at least in part, on: a first sum, wherein the first sum is obtained by adding an amplitude of a spectral peak corresponding to the fundamental frequency to amplitudes of spectral peaks in a first subset of spectral peaks in the optical sensing means signal, wherein the first subset of spectral peaks is selected from spectral peaks associated with integral multiples of the fundamental frequency in the optical sensing means signal, and a second sum obtained by adding the amplitudes of spectral peaks in a second subset of spectral peaks in the optical sensing means signal, wherein the second subset of spectral peaks is selected from a set of spectral peaks in the optical sensing means signal.

Disclosed embodiments also pertain to a computer-readable medium embodying instructions, which, when executed by a processor, perform steps in a method comprising: obtaining measurements of an optical sensor signal, the optical sensor signal measurements based, in part, on a heart rate of a user; and obtaining measurements of a motion sensor signal, the motion sensor signal measurements based, in part, on motion of the user. The method may further comprise: determining based, in part, on a comparison of a spectral peaks obtained from the optical sensor signal measurements and spectral peaks obtained from the motion sensor signal measurements, a fundamental frequency associated with the heart rate of the user in the optical sensor signal. A first heart rate of the user may be estimated based, in part, on the fundamental frequency. In some embodiments, the method may further comprise obtaining a first quality metric associated with the first heart rate. In some embodiments, the first quality metric may be based, at least in part, on: a first sum, wherein the first sum is obtained by adding an amplitude of a spectral peak corresponding to the fundamental frequency, to amplitudes of a subset of spectral peaks associated with integral multiples of the fundamental frequency in the optical sensor signal, and a second sum obtained by adding the amplitudes of a subset of spectral peaks in the optical sensor signal.

Embodiments disclosed also relate to hardware, software, firmware, and program instructions created, stored, accessed, or modified by processors using computer readable media or computer-readable memory. The methods described may be performed on processors and various user equipment.

These and other embodiments are further explained below with respect to the following figures. It is understood that other aspects will become readily apparent to those skilled in the art from the following detailed description, wherein it is shown and described various aspects by way of illustration. The drawings and detailed description are to be regarded as illustrative in nature and not as restrictive.

BRIEF DESCRIPTION OF THE DRAWINGS

Embodiments of the invention will be described, by way of example only, with reference to the drawings.

FIG. 6 shows a flowchart for a method to compute quality metrics associated with the RHR in a manner consistent with disclosed embodiments.

DETAILED DESCRIPTION

Figure 1:
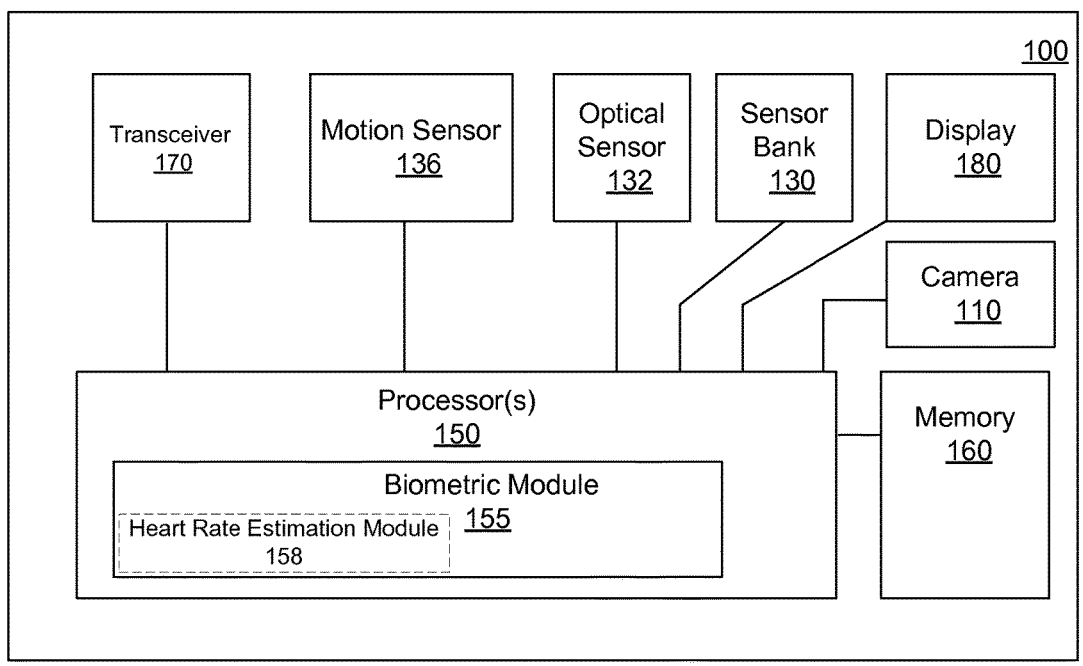
FIG. 1 shows a block diagram of exemplary device 100 capable of obtaining biometric information in a manner consistent with disclosed embodiments.

The detailed description set forth below in connection with the appended drawings is intended as a description of various aspects of the present disclosure and is not intended to represent the only aspects in which the present disclosure may be practiced. Each aspect described in this disclosure is provided merely as an example or illustration of the present disclosure, and should not necessarily be construed as preferred or advantageous over other aspects. The detailed description includes specific details for the purpose of providing a thorough understanding of the present disclosure. However, it will be apparent to those skilled in the art that the present disclosure may be practiced without these specific details. In some instances, well-known structures and devices are shown in block diagram form in order to avoid obscuring the concepts of the present disclosure. Acronyms and other descriptive terminology may be used merely for convenience and clarity and are not intended to limit the scope of the disclosure.

Biometric information may be obtained using sensors on mobile devices including wearable devices. For example, biometric information is often obtained based on measurements by optical sensors (e.g. PPG sensors). For example, user cardiovascular measurements may be used to obtain heart rate, which is used in a variety of biometric calculations. Depending on the application, heart rate can be determined 1) continuously over some period; 2) periodically, in the background; and/or 3) in one-shot mode on user demand. However, conventional cardiovascular measurements and/or heart rate determination techniques are often affected detrimentally by user movement. For example, noise bursts or noise spikes, which may be caused by abrupt or continuous user movement, can degrade the quality of signals used to make cardiovascular measurements thereby producing inaccuracies.

To compensate for user motion, motion related measurements provided by an accelerometer may be input to an adaptive filter to facilitate noise reduction. Conventionally, the adaptive filter may use the motion related signals to compensate for motion induced noise in the cardiovascular and/or heart rate signal in the time domain. However, when motion is large, the adaptive filter may not compensate adequately because the motion related signal may be an order of magnitude (or more) greater than the cardiovascular and/or heart rate signal. On the other hand, compensation may also be inadequate, for example, during sedentary activities that involve motion (e.g. typing), where the motion sensor signal may be weak.

Some disclosed embodiments improve the accuracy and/or reliability of measured signals relating to one or more cardiovascular parameters from an optical sensor based, in part, on input signal conditioning, spectral analysis and comparison of the optical and motion sensor signals and processing in the frequency domain. The measurements may be related to a user heart rate and/or used to obtain an estimate the user's heart rate. In some embodiments, one or more quality metric(s) indicative of the confidence of the proximity of the estimated heart rate to a likely actual heart rate may be obtained. The quality metric(s) may be based, in part, on parameters associated with and/or derived from spectral analysis of waveforms associated with the optical and motion sensor signals. In some embodiments, the quality metric(s) may be output along with the estimated heart rate and may be indicative of the robustness of the measurement process.

These and other techniques are further explained below with respect to the figures. It is understood that other aspects will become readily apparent to those skilled in the art from the following detailed description, wherein it is shown and described various aspects by way of illustration. The drawings and detailed description are to be regarded as illustrative in nature and not as restrictive.

FIG. 1 shows a block diagram of exemplary device 100 capable of obtaining biometric information in a manner consistent with disclosed embodiments.

In FIG. 1, device 100, may take the form of a mobile station or mobile device such as a wearable device or other device proximate to or in contact with the user's skin tissue. In some embodiments, device 100 may be in contact with an optically transparent surface, where the surface is proximate to, or in contact with the user's skin tissue. In general, the term "skin" or "skin tissue," as used herein, is used to refer to cutaneous tissue, or an optically transparent surface in contact with or in close proximity to cutaneous tissue. In addition, the term "movement relative to skin" or "movement of the sensor relative to the skin" is used to refer to movement of any body part under the optical sensor relative to the optical sensor that measures one or more cardiovascular parameters. The body parts include skin, bones, cutaneous tissue, subcutaneous tissue, etc, under the optical sensor all of which may affect measurements by the optical sensor when there is relative motion. The term "cardiovascular" is used to refer to the circulatory system including the heart, blood, and blood vessels. Measurements of one or more parameters associated with a user's cardiovascular system may be used to obtain biometric information, including a user heart rate.

In general, device 100 may take the form of a watch, wristband, ear plug, chest band, arm, shoulder, leg or ankle cuff and/or another device in contact with skin. In general, the devices and techniques disclosed herein may be used in conjunction with biometric measurements, where motion induced noise may detrimentally affect the accuracy and/or reliability of the measurements. The term "accuracy" refers to the proximity of a measurement of a parameter to an ideal or actual value of the parameter. The term "reliability" refers to the degree of variation in accuracy over a series of measurements.

In some embodiments, device 100 may provide functionality associated with a cellular phone, mobile phone, other wireless communication device and/or a wearable device coupled to a wireless communication device. For example, device 100 may be capable of or coupled to a device capable of receiving wireless communication and/or navigation signals. In some embodiments, device 100 may take the form of a wearable computing device, which may include a display 180 and/or a camera 110 paired to a wearable headset and include various other sensors. For example, the headset may include a head mounted display (HMD), which may be used to display live and/or real world images.

In some embodiments, device 100 may be a standalone biometric measurement device. The biometric measurement device may, in some instances, be incorporated into another device such as an activity tracker, gaming or other device that may not be configured to connect to a network or to otherwise communicate, either wirelessly or over a wired connection, with another device. For example, device 100 may omit communication elements and/or networking functionality. Thus, in some embodiments, all or part of one or more of the techniques described herein may be implemented in a standalone device that may not be configured to connect using wired or wireless networking with another device.

As shown in FIG. 1, an example device 100 may include motion sensor 136, optical sensor 132, sensor bank 130, display 180, one or more processor(s) 150 (hereinafter referred to as "processor(s) 150"), memory 160 and/or transceiver 170, which may be operatively coupled to each other and to other functional units (not shown) on device 100 through connections such as buses, lines, fibers, links, etc., or some combination thereof.

In some embodiments, device 100 may also optionally include camera 110, which may include charge coupled devices (CCD), complementary metal oxide semiconductor (CMOS), and/or various other image sensors. Camera(s) 110, which may be still or video cameras, may capture a series of image frames of an environment and send the captured image frames to processor 150. In some embodiments, camera(s) 110 may be external and/or housed in a wearable display 180, which may be operationally coupled to, but housed separately from, processors 150 and/or other functional units in device 100.

Transceiver 170 may, for example, include a transmitter enabled to transmit one or more signals over one or more types of wireless communication networks and a receiver to receive one or more signals transmitted over the one or more types of wireless communication networks. Transceiver 170 may facilitate communication with wireless networks based on a variety of technologies such as, Wireless Personal Area Networks (WPANs) such Bluetooth, Near Field Communication (NFC), networks based on the IEEE 802.15x family of standards, etc. In some embodiments, transceiver 170 may also facilitate communication with femtocells, Wi-Fi networks or Wireless Local Area Networks (WLANs), which may be based on the IEEE 802.11 family of standards, and/or Wireless Wide Area Networks (WWANs) such as LTE, WiMAX, etc. For example, in some embodiments, transceiver 170 may facilitate communication with another device such as a server, cell phone, and/or other computing device, which may be coupled to one or more of the various networks described above.

For example, the transceiver 170 may facilitate communication (directly or indirectly) with a WWAN such as a Code Division Multiple Access (CDMA) network, a Time Division Multiple Access (TDMA) network, a Frequency Division Multiple Access (FDMA) network, an Orthogonal Frequency Division Multiple Access (OFDMA) network, a Single-Carrier Frequency Division Multiple Access (SC-FDMA) network, Long Term Evolution (LTE), WiMax and so on. A CDMA network may implement one or more radio access technologies (RATs) such as cdma2000, Wideband-CDMA (W-CDMA), and so on. Cdma2000 includes IS-95, IS-2000, and IS-856 standards. A TDMA network may implement Global System for Mobile Communications (GSM), Digital Advanced Mobile Phone System (D-AMPS), or some other RAT. GSM, W-CDMA, and LTE are described in documents from an organization known as the "3rd Generation Partnership Project" (3GPP). Cdma2000 is described in documents from a consortium named "3rd Generation Partnership Project 2" (3GPP2). 3GPP and 3GPP2 documents are publicly available. The techniques may also be implemented in conjunction with any combination of WWAN, WLAN and/or WPAN.

For example, one or more measurements obtained by motion sensor 136 and/or optical sensor 132 on device 100 may be sent to another device, such as a mobile phone using transceiver 170. The mobile phone may process the measurements in accordance with disclosed techniques and send results back to device 100, which may be receive the results through transceiver 170. The received results may be further processed by processor (s) 150 and/or displayed using display 180.

In some embodiments, camera 110, transceiver 170 and/or one or more other ports on device 100 may be omitted. Embodiments disclosed herein may be used in a standalone device, for example, in a wearable device that does not include a camera, transceiver 170 and/or communicate with another device. Thus, in some embodiments, device 100 may obtain measurements from sensor bank 130, motion sensor 136 and/or optical sensor 132. The measurements may be processed by processor(s) 150 using biometric module 155 and/or heart rate estimation module 158 and/or based on routines stored in memory 160. The results obtained may be displayed on display 180 on device 100. Display 180 may include a screen, HMD, etc capable of rendering images, including color images. In some embodiments, display 180 and/or device 100 may be housed in a wearable device that may be coupled but housed separately from device 100.

In some embodiments, optical sensor 132 may take the form of a PPG sensor or another sensor that uses optical techniques to obtain biometric measurements. For example, the optical sensor may output electrical signals based on photometric measurements related to volumetric changes in blood vessels in skin tissue and/or other measurements of cardiovascular parameters. Various optical sensors are known and available, such as Analog Devices ADPD142RG/ADPD142RI, which are optical sensors designed to stimulate LEDs and measure the corresponding optical return signals. The optical return signals may be sent to processor(s) 150 and/or, in some instances, used to estimate some biometric information such as heart rate. Optical sensor 132 may include photodiodes and/or LEDs to output light and measure corresponding optical return signals. In some embodiments, optical sensor 132 may measure one or more parameters associated with a user cardiovascular system and provide biometric and/or heart rate related information. In some embodiments, the cardiovascular parameter measurements, biometric or heart rate related information may be provided at some specified rate. For example, optical sensor 132 may provide measured samples at a user-specified or default sampling rate to processor(s) 150. In some embodiments, the sampling rate of optical sensor 132 may be configurable. For example, for heart rate related measurements, optical sensor 132 typically provides samples at a rate greater than twice a maximum heart rate. In some embodiments, the samples provided by optical sensor 132 may be buffered in memory 160 and conditioned prior to being processed by processor(s) 150.

Further, in some embodiments, the time window over which the sample measurements are obtained may be configurable. In some embodiments, the time window may be user configurable or default to one of several options based on an operating mode of device 100. For example, the time window may be adjusted based on whether the measurements are being captured continuously, or in a "one shot" mode, expected or measured amount of user motion, and/or based on the available memory and desired response time, an/or accuracy/reliability constraints set by the user.

In some embodiments, the heart rate range, maximum heart rate and sampling interval may be user-configurable and/or set based on measurements associated with the motion sensor signal. For example, based on user settings and/or the power and frequencies of spectral peaks of the motion sensor signal, device 100 may determine whether the user is moving, in relatively low motion or motionless state, walking, jogging, running etc. and accordingly dynamically set or reset the heart rate range and likely maximum heart rate.

In some embodiments, configurable parameters may also include: 1) the number of extracted spectral optical peaks; 2) the number of extracted spectral motion peaks; 3) the minimum height of a local peak selected as a candidate peak, which improves estimation under noisy conditions; 4) a motion power parameter for customizing the motion state categories; 5) a motion spectral bandwidth parameter for categorizing the motion states into narrowband (walk or run) or more complex motions. 6) adaptive smoothing/filtering parameters related to system responsiveness; 7) clamping parameters related to sensitivity of the clamping process; 8) blanking parameters related to sensitivity of the blanking process; and 9) high pass filter parameters used during conversion of the samples into AC signals. Parameters (1) and (2) above are related to quality estimates obtained under noisy conditions.

In certain example implementations, device 100 may also include motion sensor 136, which may take the form of an Inertial Measurement Unit (IMU) and/or accelerometers. Motion sensor 136 may include one or more gyroscopes and/or one or more accelerometers. Motion sensor 136 may provide movement related information to processor(s) 150. In some embodiments, the movement related information may be provided at some specified rate. For example, motion sensor 136 may provide measured samples at a user-specified or default sampling rate to processor(s) 150. In some embodiments, the sampling rate of motion sensor 136 may be configurable. In some embodiments, the samples provided by motion sensor 136 in some predetermined or configured time window may be conditioned and buffered in memory 160 and prior to being processed by processor(s) 150. Device 100 may also include sensor bank 130, which may include various other sensors such as ambient light sensors, acoustic sensors, electro-mechanical sensors, etc.

Processor(s) 150 may execute software to process measurements by optical sensor 132, motion sensor 136 and/or sensor bank 130. Processor(s) 150 may be implemented using a combination of hardware, firmware, and software. Processor(s) 150 may represent one or more circuits configurable to perform at least a portion of a computing procedure or process related to processing sensor measurements and/or obtaining biometric information derived from the measurements. Processor(s) 150 may retrieve instructions and/or data from memory 160. In some embodiments, processor(s) 150 may comprise biometric module 155, which may execute or facilitate the execution of various biometric applications, such as the exemplary heart rate estimation module 158, as outlined in the disclosure.

In some embodiments, processor(s) 150 may include biometric module 155, which may be implemented using some combination of hardware and software. For example, in one embodiment, biometric module 155 may be implemented using software and firmware. In another embodiment, dedicated circuitry, such as Application Specific Integrated Circuits (ASICs), Digital Signal Processors (DSPs), etc. may be used to implement biometric module 155. In some embodiments, biometric module 155 may include functionality to communicate with one or more other processors and/or other components on device 100. In some embodiments, input from optical sensor 132 and motion sensor 136 and/or biometric information derived from cardiovascular measurements by optical sensor 132 and/or motion sensor 136 (e.g. as obtained by biometric module 155) may be provided to heart rate estimation module 158, which may output a heart rate and/or one or more quality metrics associated with the output heart rate. In some embodiments, the measured signals from optical sensor 132 and motion sensor 136 may be buffered in memory 160 and conditioned prior to being processed by processor(s) 150, biometric module 155, and/or heart rate estimation module 158. For example, the buffered signals may processed by clamping to remove noise spikes, passing the signals through a high pass filter to remove DC and low frequency components and analyzed statistically to discard outliers.

All or part of memory 160 may be co-located (e.g., on the same die) with processors 150 and/or located external to processors 150. Processor(s) 150 may be implemented using one or more application specific integrated circuits (ASICs), central and/or graphical processing units (CPUs and/or GPUs), digital signal processors (DSPs), digital signal processing devices (DSPDs), programmable logic devices (PLDs), field programmable gate arrays (FPGAs), controllers, micro-controllers, microprocessors, embedded processor cores, electronic devices, other electronic units designed to perform the functions described herein, or a combination thereof, to name a few examples.

Memory 160 may represent any type of long term, short term, volatile, nonvolatile, or other memory and is not to be limited to any particular type of memory or number of memories, or type of physical media upon which memory is stored. In some embodiments, memory 160 may hold code (e.g. instructions that may be executed by one or more processors) to facilitate various biometric and/or heart rate estimation methods. Memory 160 may also include buffers to store the signal measurements received from motion sensor 136 and optical sensor 132 and to store intermediate data and processed results.

In general, memory 160 may represent any data storage mechanism. Memory 160 may include, for example, a primary memory and/or a secondary memory. Primary memory may include, for example, a random access memory, read only memory, etc. While illustrated in FIG. 1 as being separate from processors 150, it should be understood that all or part of a primary memory may be provided within or otherwise co-located and/or coupled to processors 150. For example, in one embodiment, conditioned signal measurements from optical sensor 132 and/or motion sensor 136 may be stored in primary memory.

Secondary memory may include, for example, the same or similar type of memory as primary memory and/or one or more data storage devices or systems, such as, for example, flash/USB memory drives, memory card drives, disk drives, optical disc drives, tape drives, solid state drives, hybrid drives etc. In certain implementations, secondary memory may be operatively receptive of, or otherwise configurable to couple to a computer-readable medium in a removable media drive (not shown) coupled to device 100. In some embodiments, a non-transitory computer readable medium may form part of memory 160 and/or processor(s) 150.

Not all modules comprised in device 100 have been shown in FIG. 1. Further, device 100 may also be modified in various ways in a manner consistent with the disclosure, such as, by adding, combining, or omitting one or more of the functional blocks shown. For example, in some configurations, device 100 may not include transceiver 170. In some embodiments, portions of device 100 may take the form of one or more chipsets, and/or the like.

Figure 2:
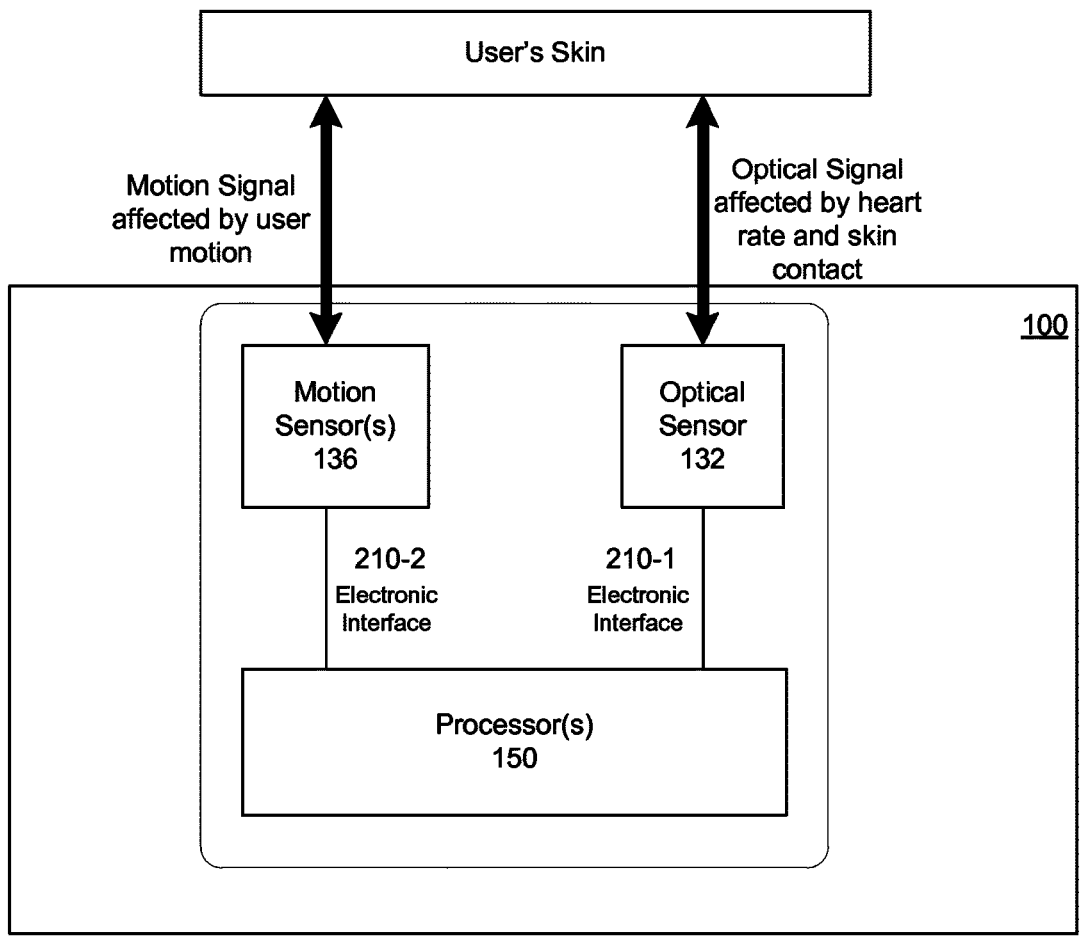
FIG. 2 shows a device with an optical sensor, which may measure and output optical signal samples related to volumetric measurements of blood vessels near the skin surface.

FIG. 2 shows device 100 with optical sensor 132, which may measure and output optical signal samples related to volumetric measurements of blood vessels near the skin surface. The optical signal measurement samples may be input to one or more of processor(s) 150, biometric module 155 and/or heart rate estimation module 158. Because of user movements, samples from optical sensor signal measurements 305 may vary and/or contain noise or other artifacts. For example, if the amount of skin contact varies the quality of the optical sensor signal measurements may be affected.

In some embodiments, motion sensor 136 may measure motion relative to skin and output signal samples dependent on the motion. In some embodiments, signals from both optical sensor 132 and motion sensor 136 may be output via electronic interfaces 210-1 and 210-2, respectively, to processor(s) 150. In some embodiments, electronic interfaces 210-1 and 210-2 may perform a portion of the conditioning of signals from optical sensor 132 and motion sensor 136 optical sensor 132 and motion sensor 136.

Figure 3:
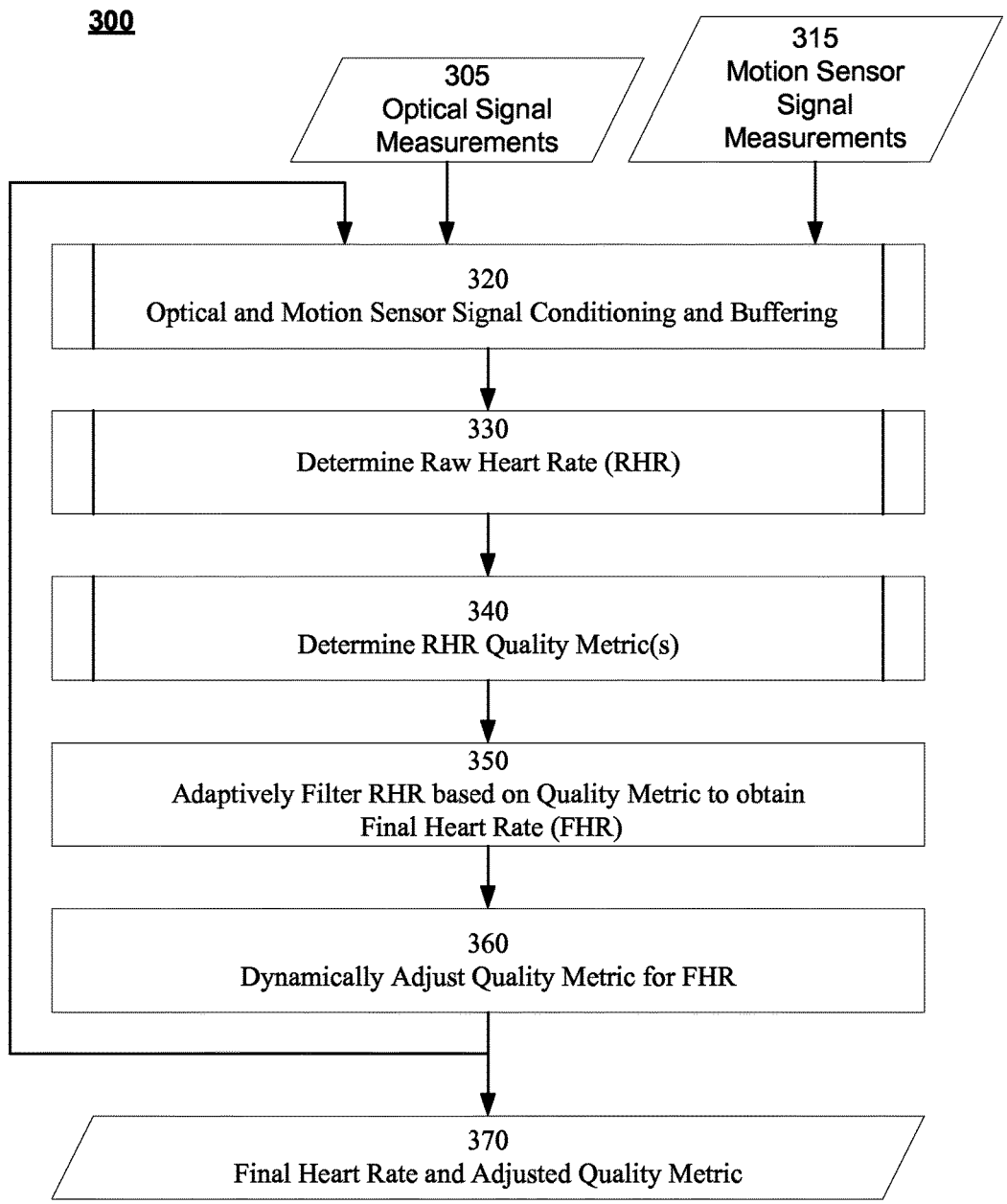
FIG. 3 shows a flowchart depicting an exemplary method of obtaining biometric information such as heart rate based on optical and motion sensor signal measurements in a manner consistent with disclosed embodiments.

FIG. 3 shows a flowchart depicting an exemplary method 300 of obtaining biometric information such as heart rate based on optical and motion sensor signal measurements in a manner consistent with disclosed embodiments. In some embodiments, portions of method 300 may be performed by device 100 using one or more of processor(s) 150, biometric module 155 and/or heart rate estimation module 158 based, in part, on cardiovascular parameter measurements received from optical sensor 132, and measurements by motion sensor 136.

In some embodiments, optical and motion sensor signals may be sampled periodically to obtain optical sensor signal measurements 305 and motion sensor signal measurements 315. In Optical and Motion Sensor Signal Conditioning and Buffering block 320, measured signal samples including optical sensor signal measurements 305 and motion sensor signal measurements 315 may be conditioned and buffered.

Figure 4:
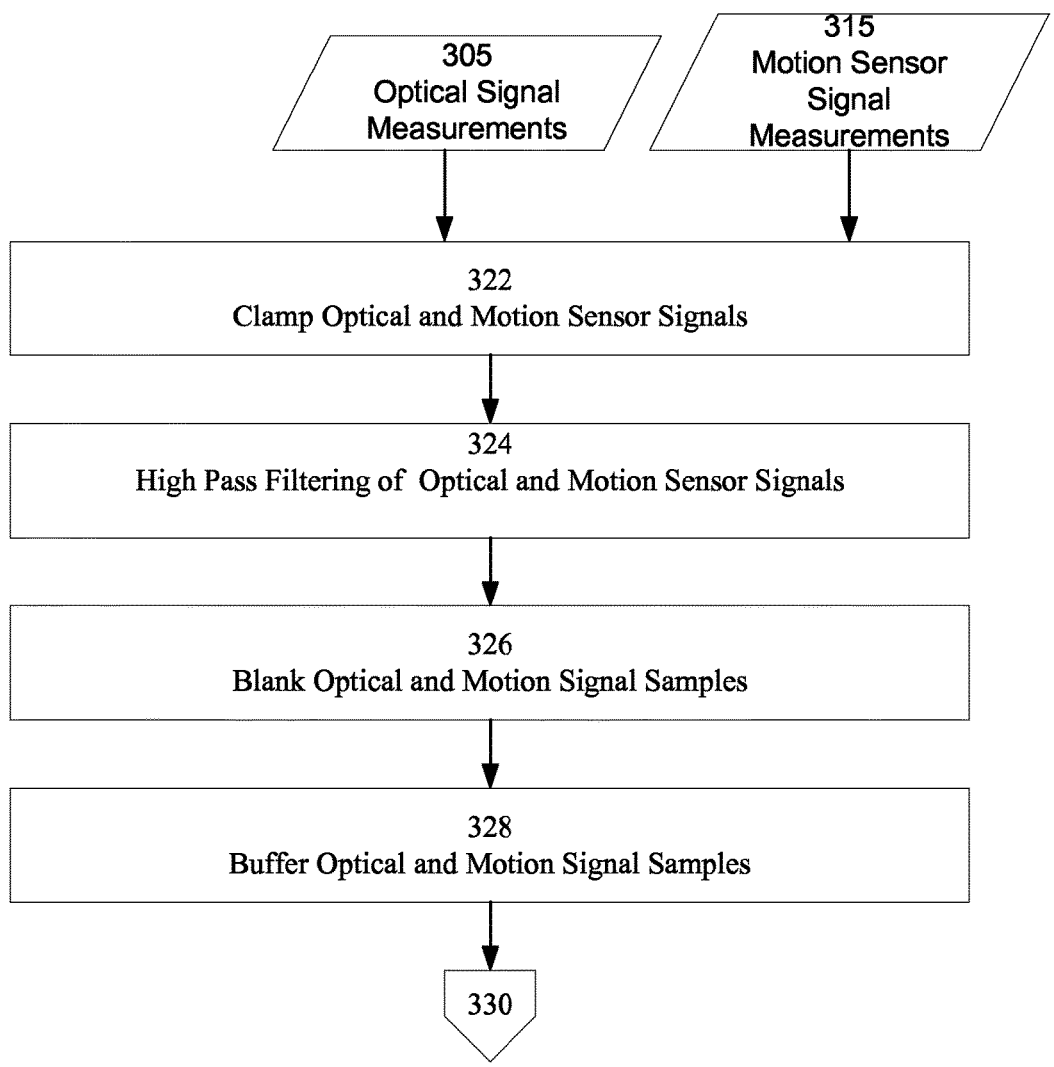
FIG. 4 shows a flowchart depicting an exemplary method to condition and buffer optical and motion sensor signals consistent with disclosed embodiments.

FIG. 4, which pertains to Optical and Motion Sensor Signal Conditioning and Buffering block 320, shows a flowchart depicting an exemplary method to condition and buffer optical and motion sensor signals consistent with disclosed embodiments. For example, as shown in FIG. 4, in step 322, optical and motion sensor signals may be clamped to mitigate the effects of noise spikes. Next, in step 324, a high pass filter may be applied to the clamped optical and motion sensor signals to remove the DC signal and/or any low frequency components.

In step 326, the clamped and filtered optical and motion sensor signals may be "blanked". During "blanking", a time window over which signal measurements were obtained may be divided into time segments and the clamped and filtered signals within each time segment are analyzed statistically (e.g. by computing a minimum, maximum and other statistical measures for each signal segment). Time segments considered to be outliers may be discarded and/or replaced with "zero" signal values so that the discarded/zeroed outlier segments do not contribute to determination of a first heart rate or raw heart rate (RHR). For example, a time segment (for the optical sensor signal) may determined to be an outlier if the spread or difference between the maximum and minimum optical sensor signal values exceeds a first predetermined or statistically determined threshold. Similarly, a time segment (for the motion sensor signal) may be determined to be an outlier if the spread or difference between the maximum and minimum optical sensor signal values exceeds a second predetermined or statistically determined threshold.

In step 328, the conditioned optical and motion sensor signals may be buffered. For example, in some embodiments, the conditioned optical and motion sensor signals may be stored in buffers that are part of memory 160. Thus, the output of step 326 may be an input signal buffer comprising conditioned PPG and motion sensor signal measurements. Upon completion, control may be returned to method 300 at step 330.

Referring to FIG. 3, in block 330, the Raw Heart Rate (RHR) may be determined. The term "Raw Heart Rate" as used herein is used to refer to an estimate of a first heart rate, which may be obtained, based on the conditioned and buffered optical sensor and motion sensor signals.

Figure 5:
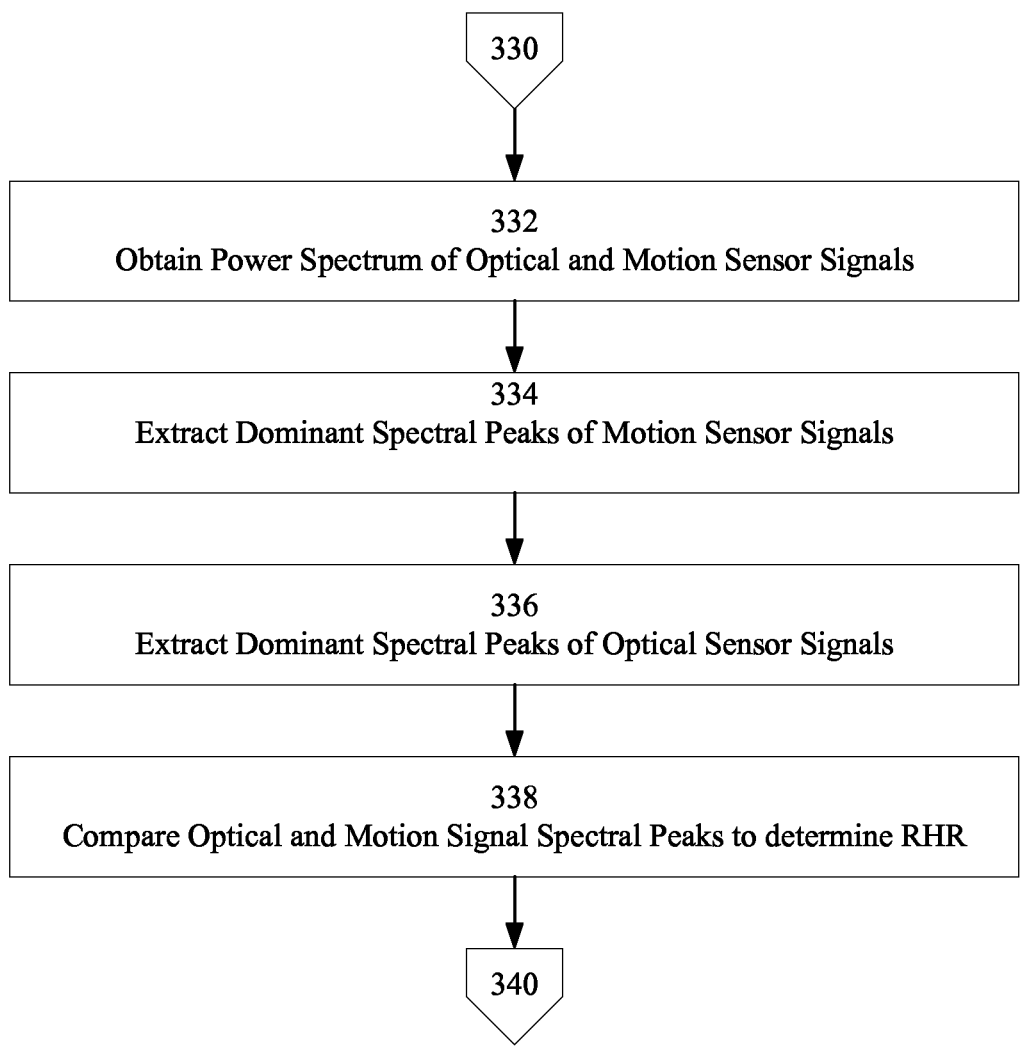
FIG. 5, which shows a flowchart for a method to compute the RHR in a manner consistent with disclosed embodiments.

Block 330 is further detailed in FIG. 5, which shows a flowchart for a method to compute the RHR. For example, as shown in FIG. 5, in step 332, power spectra corresponding to (i) the optical and (ii) the motion sensor signal measurements may be obtained. In one embodiment, Fast Fourier Transform (FFT) based techniques may be used on the optical and motion sensor input signal samples to obtain a frequency domain representation of the input signals. The magnitudes of the FFT of the input optical and motion signals may be squared to obtain the corresponding power spectrum for each signal. Techniques other than simple FFT such as non-parametric methods such as Welch's method, or parametric methods, such as autoregressive model estimation, may be used to obtain the power spectrum of the conditioned optical and motion sensor signals in the input buffer.

In step 334, a set of dominant or largest amplitude motion sensor spectral peaks is extracted from the motion sensor power spectrum obtained in step 332.

Figure 7:
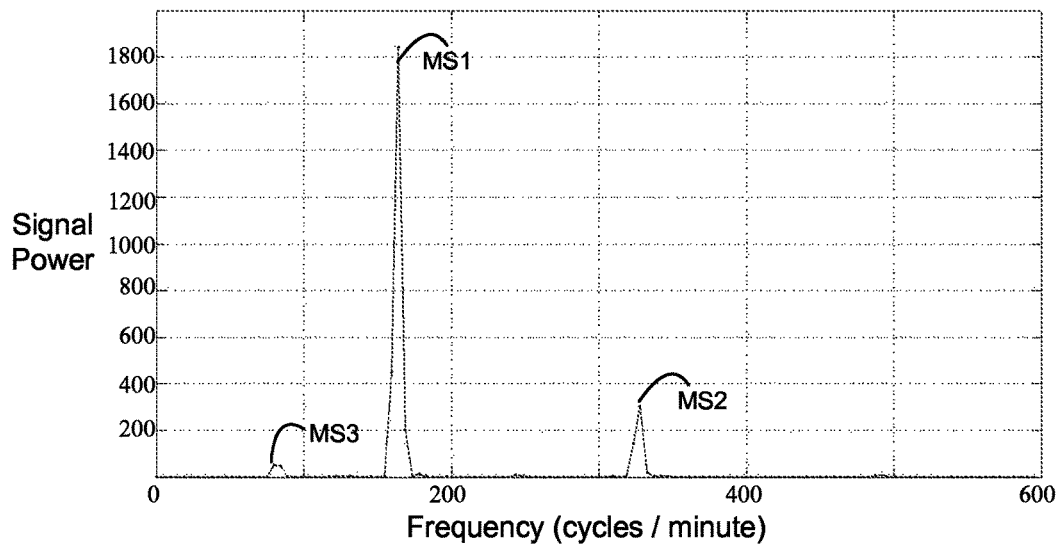
FIG. 7 shows an exemplary Motion Sensor Power Spectrum illustrating the variation in motion sensor signal power (Y-axis) relative to frequency in cycles per minute (X-axis).

FIG. 7 shows an exemplary Motion Sensor Power Spectrum 700 showing the variation in motion sensor signal power (Y-axis) relative to frequency in cycles per minute (X-axis). For example, Motion Sensor Power Spectrum 700 may be obtained in step 332 (in FIG. 5). As shown, in FIG. 7, Motion Sensor Power Spectrum may include dominant spectral peaks identified by labels MS1, MS2 and MS3 in FIG. 7.

As an example, MS1 may represent a frequency associated with steps taken by a user while jogging. MS2 may be a harmonic at twice the frequency of MS1. Further, MS3 may represent the motion of another body part. For example, if device 100 is worn or the user's hand or arm, MS3 may represent the frequency associated with movement of the arm while jogging, which may occur at approximately half the frequency of steps.

Referring to FIG. 5, in step 336, a set of dominant or largest amplitude optical sensor spectral peaks may be extracted from the optical sensor power spectrum obtained in step 332.

Figure 8:
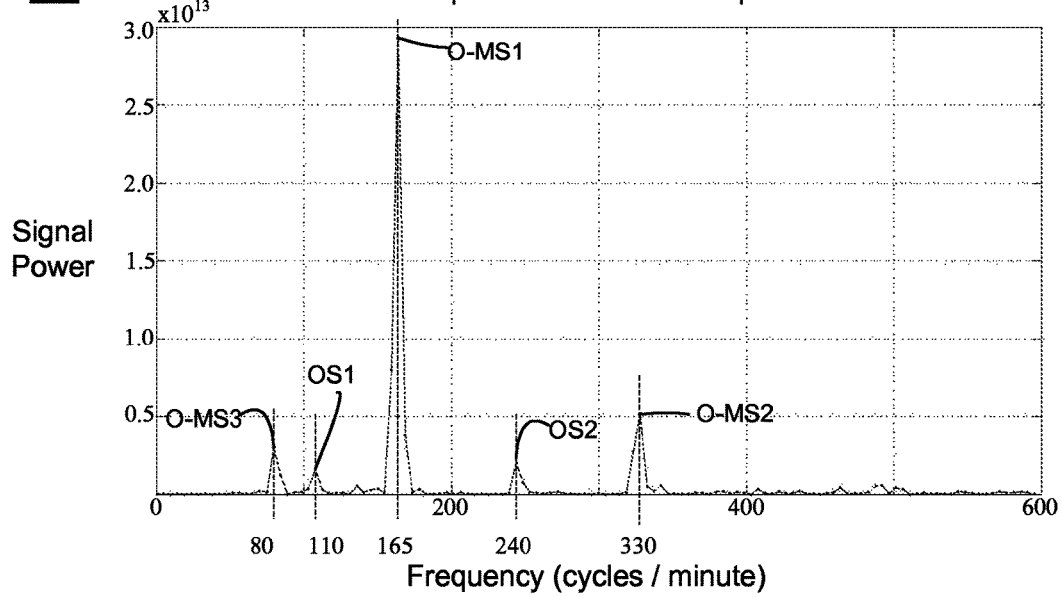
FIG. 8 shows an exemplary Optical Sensor Power Spectrum illustrating the variation in optical sensor signal power (Y-axis) relative to frequency in cycles per minute (X-axis).

FIG. 8 shows an exemplary Optical Sensor Power Spectrum 800 showing the variation in optical sensor signal power (Y-axis) relative to frequency in cycles per minute (X-axis). With regard to FIGS. 7 and 8, the relative strengths of motion peaks in the motion sensor power spectrum (as shown in FIG. 7) may vary from the relative strength of the corresponding motion induced peak in the optical signal (as shown in FIG. 8).

In some embodiments, Optical Sensor Power Spectrum 800 may be obtained in step 332 (in FIG. 5). Further, as shown in FIG. 8, Optical Sensor Power Spectrum 800 may include dominant spectral peaks identified by labels OS1, OS2, O-MS1, O-MS2 and O-MS3 in FIG. 8.

Referring to FIG. 5, in step 336, the sets of optical and motion sensor spectral peaks may be compared to determine the RHR. For example, in one embodiment, spectral peaks in the optical sensor signal that are near in frequency to spectral peaks in the motion sensor signal may be considered as motion related. For example, (Referring to FIGS. 7 and 8), in step 336, Motion Sensor Power Spectrum 700 may be compared with Optical Sensor Power Spectrum 800. As a result of the comparison, spectral peaks O-MS1, O-MS-2 and O-MS3 in Optical Sensor Power Spectrum 800 (FIG. 8), which are close in frequency to spectral peaks MS1, MS2 and MS3 in Motion Sensor Power Spectrum 700 (FIG. 7), may be attributed to motion.

Further (Referring to FIG. 5), in step 336, optical sensor spectral peaks within some predetermined bounds (e.g. representing a likely heart rate range) that are unrelated in frequency may be attributed to heart rate, while outliers may be thought of as noise. For example, (Referring to FIG. 8) dominant peaks OS1 and OS2 may be attributed heart rate. For example, OS1 may used as a first or RHR estimate. OS2 may then be determined to be a first harmonic of OS1.

Thus, in some embodiments, the comparison of the spectral peaks in the optical sensor spectral peak set and the motion sensor spectral peak set in step 336 (FIG. 5) may yield spectral peaks that are related to: (i) noise; (ii) motion and (iii) RHR estimate. Upon completion, of block 330, control may be returned to method 300 at step 340. In some embodiments, the comparison of spectral peaks may be used to determine a fundamental frequency in the optical sensor signal, which, in turn, may be used to obtain a first heart rate estimate for a user (e.g. RHR). The term "fundamental frequency," as used herein, refers to a fundamental frequency in the optical sensor signal that may be associated with and/or indicative of a user heart rate, such as, for example, the RHR.

In some embodiments, the RHR may be estimated based, in part, on the fundamental frequency. For example, a frequency domain representation of the optical sensor signal may be obtained from a plurality of optical sensor signal measurements (which may be in the time domain). Similarly, a frequency domain representation of the motion sensor signal may be obtained from a plurality of motion sensor signal measurements (which may be in the time domain). Further, spectral peaks obtained from the optical sensor signal measurements may be compared to spectral peaks obtained from the motion sensor signal measurements to determine non-motion related spectral peaks in the frequency domain representation of the optical sensor signal. Next, based on the non-motion related spectral peaks in the frequency domain representation of the optical sensor signal, the fundamental frequency associated with the heart rate of the user may be determined.

Referring to FIG. 3, in some embodiments, in block 340 quality metrics associated with the RHR may be determined. The quality metrics may provide an indication of the accuracy and/or reliability of RHR. The RHR quality measure may be used to provide a confidence level in the estimated RHR. In some embodiments, the quality metrics may be determined based, in part, on spectral features associated with the power spectrum of the optical sensor. In some embodiments, the quality metric(s) may be independent of signal shape.

Block 340 is further detailed in FIG. 6, which shows a flowchart for a method to compute quality metrics associated with the RHR determined in step 330. For example, as shown in FIG. 6, in step 342, in some embodiments, a first RHR quality metric may be computed based on: (i) the power of the fundamental frequency and harmonics of the fundamental frequency, relative to (ii) non-motion related power content in the optical sensor signal. For example, in step 342, a first RHR quality metric may be computed as the ratio of: (a) the sum of the amplitude of the fundamental frequency in the optical sensor spectrum and amplitudes of a subset of optical sensor spectral peaks that are integral multiples of the fundamental frequency; to (b) the sum of amplitudes of a subset of non-motion related spectral peaks. For example, in some embodiments, the subset of optical sensor spectral peaks that are integral multiples of the fundamental frequency may include those optical sensor spectral peaks that are above some threshold power value. In some embodiments, the subset of non-motion related spectral peaks may be selected from a set of spectral peaks and include those spectral peaks in the optical sensor signal that are above some threshold power value. When the threshold is zero in either case above, all non-motion related spectral peaks may be included in the computation of the first quality metric. In some embodiments, some specified number of non-motion related spectral peaks in the optical sensor signal may be included in the subset of non-motion related spectral peaks.

In some embodiments, a first quality metric may be obtained as:

$$Q1_{RHR} = \frac{\sum\limits_{P_i \; s.t. |f_i - kF_0| < \varepsilon_k} a_i}{\sum\limits_{P_i} a_i} \quad (1)$$

where, $Q1_{RHR}$ is a quality metric associated with the RHR estimate; $a_i$ is the amplitude, and $f_i$ is the frequency of the $i^{th}$ spectral peak $P_i$ in the optical sensor signal, where $1 \le i \le n$, and $i = 1, 2, 3, \ldots n$, is a non-negative integer; $F_O$ is the fundamental frequency of the optical sensor signal; $k(F_O)$ is the $k^{th}$ multiple of the fundamental frequency; and the term $P_i$ s.t. $|f_i - kF_0| < \varepsilon_k$ represents those peaks $P_i$ in the optical sensor signal such that ("s.t.") their corresponding frequencies $f_i$ is within some threshold $\varepsilon_k$ of $k(F_O)$, $1 \le k \le k_{max}$. In some embodiments, the threshold $\varepsilon_k$ may be varied as k increases. In other embodiments, the threshold $\varepsilon_k$ may be set to some fixed value, such as, for example, $\varepsilon_{k_{max}}$. In some embodiments, k may take non-negative integer values, for example, $k = 0, 1, 2, 3 \ldots k_{max}$. In some embodiments, k may one or more fractional values, for example, $k = 0, (\frac{1}{2}), 1, 2, 3, 4 \ldots k_{max}$; or, $k = 0, (\frac{1}{2}), 1, (3/2), 2, (5/2), 3, (7/2) \ldots k_{max}$. The term $|f_i - kF_0|$ represents the absolute value of the difference between $f_i$ and $kF_0$.

Figure 9:
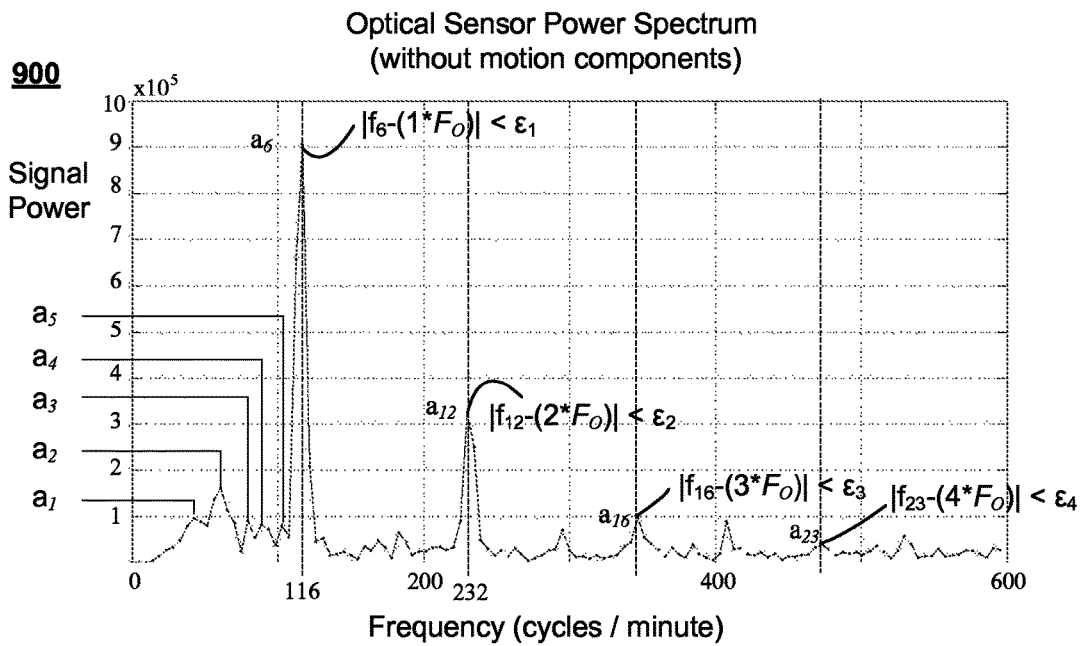
FIG. 9 shows an exemplary Optical Sensor Power Spectrum without motion related spectral components.

FIG. 9 shows Optical Sensor Power Spectrum 900 without motion related spectral components. In FIG. 9, the X-axis represents Frequency in cycles per minute while the Y-axis represents Signal Power. In some embodiments, Optical Sensor Power Spectrum 900 may be obtained, by removing motion related components from Optical Sensor Power Spectrum 800 (e.g. after comparison of Motion Sensor Power Spectrum 700 and Optical Sensor Power Spectrum 800 in step 338 of FIG. 5).

In FIG. 9, the fundamental frequency of the optical sensor signal is shown as $F_O = RHR \approx 116$ cycles per minute. Harmonics of $F_O$ with frequencies $(2*F_O), (3*F_O), (4*F_O), \ldots$ are also shown in FIG. 9. Further, FIG. 9 also shows the amplitudes of spectral peaks $a_1, a_2, a_3, a_4, a_5, a_6 \ldots$, which may correspond to frequencies $f_1, f_2, f_3, f_4, f_5, f_6 \ldots$, respectively, of the optical sensor signal. As shown in FIG. 9, the sixth non-motion related spectral peak with amplitude $a_6$ at frequency $f_6$ may be determined to correspond to fundamental frequency $F_O$ because $P_6$ is s.t. $|f_6 - (1)F_0| < \varepsilon_1$, for $i = 6$ and $k = 1$. Similarly, the twelfth non-motion spectral peak with amplitude $a_{12}$ at frequency $f_6$ may be determined to correspond to the second harmonic of the fundamental frequency $F_O$ because $P_{12}$ is s.t. $|f_{12} - (2)F_0| < \varepsilon_2$, for $i = 12$ and $k = 2$. The third and fourth harmonics may be similarly determined because $P_{16}$ is s.t. $|f_{16} - (3)F_0| < \varepsilon_3$, for $i = 16$ and $k = 3$, and $P_{23}$ is s.t. $|f_{23} - (4)F_0| < \varepsilon_4$, for $i = 23$ and $k = 4$, respectively.

As an example, for a case without motion, the optical sensor spectral peaks are likely related either to the RHR or to noise. Typically, because the RHR is quasi-periodic, the RHR related optical sensor spectral peaks will be in harmonic ratio and the sum $$\sum\limits_{P_i \; s.t. |f_i - kF_0| < \varepsilon_k} a_i$$

(the numerator of equation 1) approaches 1. Thus, if there is zero or low power in noise peaks, then, $$\left( \sum\limits_{P_i \; s.t. |f_i - kF_0| < \varepsilon_k} a_i \right) \approx \sum\limits_{P_i} a_i,$$

so that the quality metric $Q1_{RHR}$ approaches one. Otherwise, as noise increases, the quality measure decreases and eventually approaches zero. For the general case, when there is both noise and motion, the quality metric $Q1_{RHR}$ may be based on the ratio in equation (1) above (without consideration of motion induced spectral peaks). In some embodiments, the quality measure may be independent of specific electronic and filter responses i.e. independent of shape of PPG signals.

Referring to FIG. 6, in step 344, a second quality metric may be obtained. In some embodiments, a second quality metric $Q2_{RHR}$ may be based, in part, on the width of the peak. For example, in some embodiments, second quality metric $Q2_{RHR}$ may be obtained as a ratio of: (i) a first power corresponding to the power of the spectral peak associated with the fundamental frequency divided by (ii) the sum of a) the power of the spectral peak associated with the fundamental frequency (the first power); and b) a second power corresponding to the power of the spectrum at some predetermined spectral distance to the spectral peak associated with the fundamental frequency. The "spectral distance" is used to refer to frequencies at $f+\delta$ and $f-\delta$ at distance $\delta$ from a frequency f. In one embodiment, the spectral distance $\delta$ may be predetermined and the value of $\delta$ may be set based on: an operating mode of device 100, or as a default value, and/or be configurable. In some embodiments, the second quality metric $Q2_{RHR}$ may be used as a multiplicative factor to first spectral energy based quality metric $Q1_{RHR}$. Accordingly, $Q2_{RHR}$ be defined as $$Q2_{RHR} = \frac{a_{F_O}}{a_{(F_O - \delta)} + a_{F_O} + a_{(F_O + \delta)}} \quad (2)$$

where $Q2_{RHR}$ is a second quality metric associated with the raw heart rate, $a_{F_O}$ is the amplitude associated with the fundamental frequency $F_O$, and amplitudes $a_{(F_O - \delta)}$ and $a_{(F_O +}$ δ) are associated with frequencies $F_O-\delta$ and $F_O+\delta$ at spectral distance "δ" (along the frequency axis) from fundamental frequency $F_O$.

Figure 10:
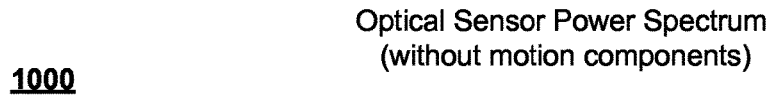
FIG. 10 shows the amplitude of the spectral peak associated with Fundamental Frequency $F_O$ of the optical sensor signal.

FIG. 10 shows the amplitude $a_{F_O}$ of the spectral peak associated with fundamental frequency $F_O$ of the optical sensor signal. As shown in FIG. 10, for the spectral peak associated with the fundamental frequency $F_O$, signal amplitudes $a_{(F_O-\delta)}$ and $a_{(F_O+\delta)}$ are associated with frequencies $F_O-\delta$ and $F_O+\delta$ at spectral distance "δ" (along the frequency axis) from fundamental frequency $F_O$. If the peak is sharp, then, as shown in FIG. 10, the signal amplitudes $a_{(F_O-\delta)}$ and $a_{(F_O+\delta)}$ fall away quickly and may be close to zero at spectral distance δ from fundamental frequency $F_O$. Therefore, $Q2_{RHR}$ approaches 1 if the spectral peak associated with the fundamental frequency is pronounced or well-defined. On the other hand, if the spectral peak associated with fundamental frequency $F_O$ is weak or not well defined, then, the signal amplitudes $a_{(F_O-\delta)}$ and $a_{(F_O+\delta)}$ associated with frequencies $F_O-\delta$ and $F_O+\delta$ may be non-trivial and the value of quality metric $Q2_{RHR}$ is lowered.

Referring to FIG. 6, in step 346, in some embodiments, first quality metric $Q1_{RHR}$ and second quality metric $Q2_{RHR}$ may be combined to obtain a third or overall RHR quality metric $Q3_{RHR}$. For example, as one example, second quality metric $Q2_{RHR}$ may be used as a multiplicative factor to modify first RHR quality metric $Q2_{RHR}$. As a simple example, the third quality metric $Q3_{RHR}$ may be obtained as $$Q3_{RHR} = Q2_{RHR} * Q1_{RHR} \quad (3)$$

In some embodiments, one or more of steps 344 and 346 may be optionally performed. In some embodiments, block 340 may output one or more of $Q1_{RHR}$, $Q2_{RHR}$, $Q3_{RHR}$. In some embodiments, $Q3_{RHR}$, which may be a mathematical combination of $Q1_{RHR}$ and $Q2_{RHR}$, may be output. Upon completion of block 340, control may be returned to method 300 (FIG. 3) at step 350.

Referring to FIG. 3, in step 350, $Q3_{RHR}$ (which may be some mathematical combination the first quality metric $Q1_{RHR}$ and the second quality metric $Q2_{RHR}$) may be used to adaptively smooth the RHR to provide a second heart rate or Final Heart rate (FHR) estimate. In one embodiment, a first order recursive filter with time changing weights may be used for adaptive smoothing. For example, the weights may be varied in proportion to one or more of the RHR quality measures at that time. In some embodiments, the FHR may be obtained by adaptively smoothing the RHR, where coefficients of an adaptive filter (which may perform the adaptive smoothing) may be adjusted based, in part, on the third quality metric.

In some embodiments, a first order adaptive smoothing filter may be used. The first order adaptive smoothing filter may use a time varying parameter, which may be based, at least partially, on: (i) $Q3_{RHR}$, the third quality metric at a time step and (ii) a non-linear constraint to determine the amount of change in heart rate at a time step relative to the adaptively smoothed heart rate at the immediately prior time step.

In some embodiments, a first order adaptive smoothing filter may receive, as input, (i) $RHR_{t_j}$, the current raw heart rate at time step $t_j$, (ii) $FHR_{t_{j-1}}$, a prior adaptively smoothed heart rate at time $t_{j-1}$, (iii)

$$Q3_{RHR_{t_j}},$$

the third quality metric at time $t_j$, and (iv) one or more parameters that may be used to determine the extent of change of the prior adaptively smoothed heart rate. For example, when the quality metric $$Q3_{RHR_{t_j}}$$

is low, a first parameter may be used to set a bound on any changes to (or control a rate of change of) $FHR_{t_j}$, the heart rate output by the adaptive smoothing filter at time step $t_j$ relative to $FHR_{t_{j-1}}$. As another example, when the quality metric $$Q3_{RHR_{t_j}}$$

is high, a second parameter may be used to set a bound on any changes to (or control a rate of change of) $FHR_{t_j}$, the heart rate output by the adaptive smoothing filter at time step $t_j$ relative to $FHR_{t_{j-1}}$. Various other parameters such as parameters related to harmonicity of the optical sensor signal may also be used in addition to the parameters outlined above to adaptively smooth the RHR and determine heart rate output by the adaptive smoothing filter.

The quality metric (e.g. $Q3_{RHR}$) may be high even in situations with high motion if, for example, the optical sensor heart rate signal is strong. When the quality metric (e.g. $Q3_{RHR}$) is high, the adaptive filter performing the adaptive smoothing may respond quickly to changes in heart rate seen in the RHR and provide corresponding updates to the FHR. On the other hand, if there is weak optical heart rate signal, then the quality metric (e.g. $Q3_{RHR}$) may be lower. When the quality metric (e.g. $Q3_{RHR}$) is low, then the adaptive filter may modify the adaptive smoothing to slow corresponding updates to the FHR estimate thereby reducing the effect of spurious emissions and errors. Embodiments disclosed may use various methods of adaptive smoothing. For example, in one embodiment, the adaptive filter may take the form of a modified, time varying, nonlinear first order recursive adaptive filter. In addition to the quality metric determined filtering parameter (e.g. $Q3_{RHR}$) described above, the modified time varying nonlinear first order recursive adaptive filter may also include parameters to limit the maximum change in FHR relative to a current FHR over some time period. By limiting the maximum change in FHR relative to a current FHR, the modified time varying nonlinear first order recursive adaptive filter may reject or minimize artifacts caused by variations in the RHR due to spurious emissions and/or errors in noisy conditions.

Next, in block 360, in some embodiments, the RHR and FHR may be compared, and a fourth quality metric $Q4_{RHR}$ may be obtained dynamically based on the results of the comparison. For example, if the absolute difference between RHR and FHR exceeds some threshold, the reported quality may be lowered. As one example, $$Q4 = \begin{cases} Qk_{RHR}, & \text{if } |RHR - FHR| \leq t \\ Qk_{RHR} * (1 - (|RHR - FHR| - t)) \end{cases}, \quad (4)$$

where $k = 1, 2, 3$

Thus, in one embodiment, according to equation (4), Q4 will retain any prior value $Qk_{RHR}$ (which may be one of $Q1_{RHR}$ (for k=1); $Q2_{RHR}$ (for k=2); or $Q3_{RHR}$ (for k=3)), when $|RHR-FHR| \leq t$. However, as the absolute value of the difference between RHR and FHR (|RHR−FHR|) increases, Q4 will dynamically and progressively reduce the prior value of $Qk_{RHR}$. Note that equation (4) is merely one method of dynamically altering the quality metric in response to the absolute value of the difference between RHR and FHR. In general, various other functions may used to determine how the quality metric is adjusted.

In block 370, the FHR and/or Q4 may be reported to the user. For example, a visual indication of the FHR and the quality metric may be provided. An actual FHR value and quality metric may be displayed on display 180. As another example, a graphic or color coded bar or chart may be displayed along with or instead of the FHR value and quality metric. In some embodiments, the user may be provided with tactile feedback to indicate certain conditions. For example, device 100 may vibrate when a specified heart rate is reached, or to indicate an error condition.

The methodologies described herein may be implemented by various techniques depending upon the application. Any machine-readable medium tangibly embodying instructions may be used in implementing the methodologies described herein. For example, software code may be stored in memory 160 and executed by a processor 150. In some embodiments, the functions may be stored as one or more instructions or code on a computer-readable medium. Examples include computer-readable media encoded with a data structure and computer-readable media encoded with a computer program. Computer-readable media includes physical computer storage media.

Figure 11:
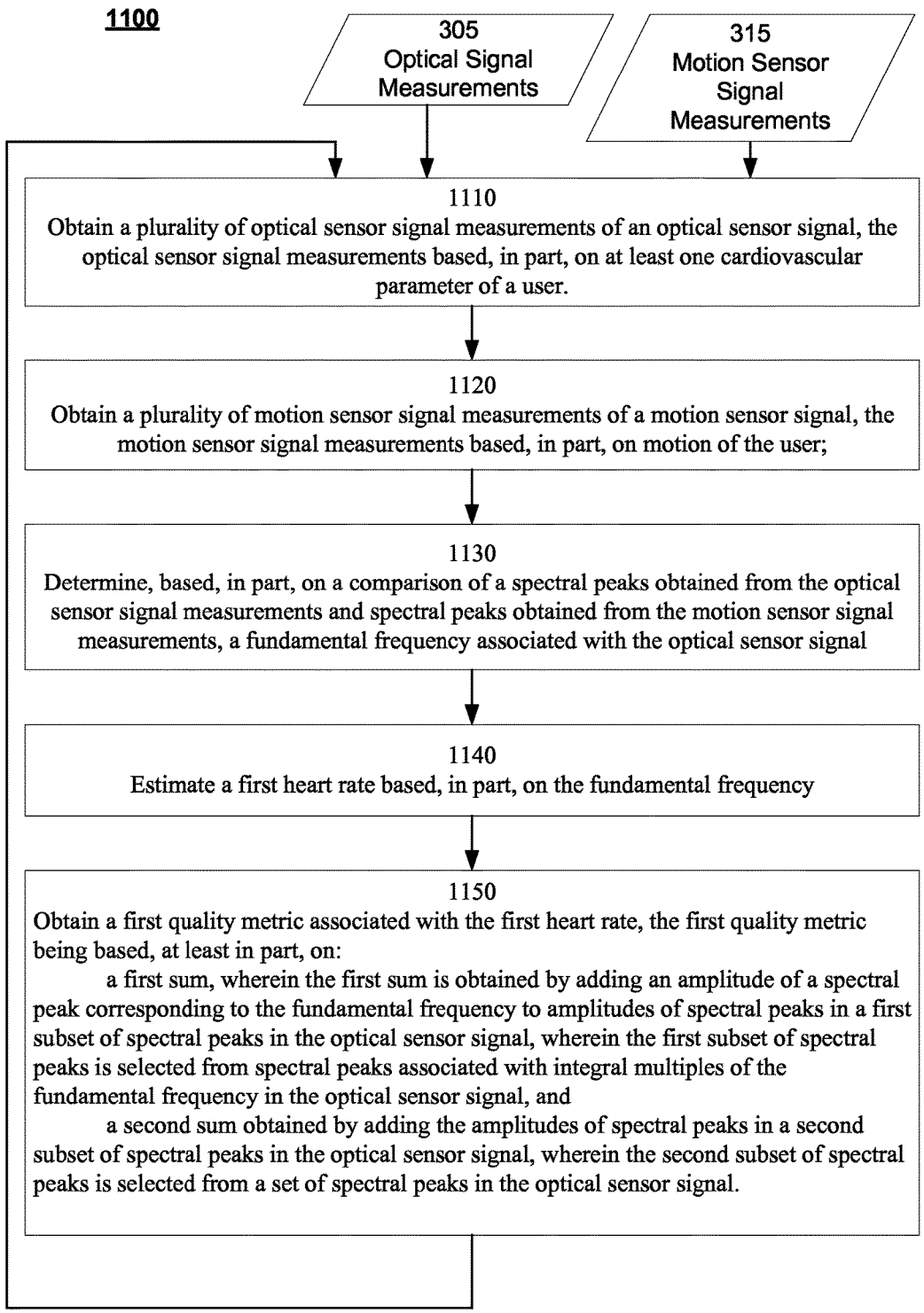
FIG. 11 shows an exemplary method for measurement shows a flowchart depicting an exemplary method of obtaining biometric information such as heart rate based on optical and motion sensor signal measurements in a manner consistent with disclosed embodiments.

FIG. 11 shows an exemplary method for measurement shows a flowchart depicting an exemplary method of obtaining biometric information such as heart rate based on optical and motion sensor signal measurements in a manner consistent with disclosed embodiments. In some embodiments, portions of method 1100 may be performed by device 100 using one or more of processor(s) 150, biometric module 155 and/or heart rate estimation module 158 based, in part, on cardiovascular parameter measurements received from optical sensor 132, and measurements by motion sensor 136. In some embodiments, optical and motion sensor signals may be sampled periodically to obtain optical sensor signal measurements 305 and motion sensor signal measurements 315.

In some embodiments, in step 1110, a plurality of optical sensor signal measurements of an optical sensor signal may be obtained. For example, the optical sensor signal measurements may be based, in part, on at least one cardiovascular parameter of a user.

Next, in step 1120, a plurality of motion sensor signal measurements of a motion sensor signal may be obtained. For example, the motion sensor signal measurements may be based, in part, on motion of the user.

In step 1130, spectral peaks obtained from the plurality of optical sensor signal measurements and spectral peaks obtained from the plurality of motion sensor signal measurements may be compared to determine a fundamental frequency associated with the optical sensor signal. In some embodiments, to determine the fundamental frequency, a frequency domain representation of the optical sensor signal may be obtained from the plurality of optical sensor signal measurements and a frequency domain representation of the motion sensor signal may be obtained from the plurality of motion sensor signal measurements. Further, spectral peaks in the frequency domain representation of the optical sensor signal may be compared to spectral peaks in the frequency domain representation of the motion sensor signal to determine one or more non-motion related spectral peaks in the frequency domain representation of the optical sensor signal. The one or more non-motion related spectral peaks in the frequency domain representation of the optical sensor signal may be used to determine the fundamental frequency associated with the optical sensor signal.

In step 1140, a first heart rate may be estimated based, in part, on the fundamental frequency.

In step 1150, a first quality metric associated with the first heart rate may be obtained. In some embodiments, the first quality metric may be based, at least in part, on: a first sum, wherein the first sum is obtained by adding an amplitude of a spectral peak corresponding to the fundamental frequency to amplitudes of spectral peaks in a first subset of spectral peaks in the optical sensor signal, wherein the first subset of spectral peaks is selected from spectral peaks associated with integral multiples of the fundamental frequency in the optical sensor signal, and a second sum obtained by adding the amplitudes of spectral peaks in a second subset of spectral peaks in the optical sensor signal, wherein the second subset of spectral peaks is selected from a set of spectral peaks in the optical sensor signal. In some embodiments, the first quality metric may be computed as a ratio of the first sum to the second sum.

In some embodiments, the method may further comprise: obtaining a second quality metric associated with the first heart rate. In some embodiments, the second quality metric may be based, in part, on: a first power corresponding to a power of the spectral peak associated with the fundamental frequency, and a second power corresponding to a power at a predetermined spectral distance from the fundamental frequency. For example, the second quality metric may be obtained as a ratio of the first power to a sum obtained by adding the first power to the second power.

In some embodiments, the method may further comprise obtaining a third quality metric based, in part, on a mathematical combination of the first quality metric and the second quality metric. Further, a second heart rate may be estimated by performing adaptive smoothing of the first heart rate, wherein the adaptive smoothing is based, in part, on the third quality metric. In some embodiments, the method may further comprise obtaining a fourth quality metric, wherein the fourth quality metric is dynamically obtained based, in part, on a comparison of the first heart rate and the second heart rate. In some embodiments, upon completion of step 1150, control may be returned to method 1100 at step 1110.

The previous description of the disclosed aspects is provided to enable any person skilled in the art to make or use the present disclosure. Various modifications to these aspects will be readily apparent to those skilled in the art, and the generic principles defined herein may be applied to other aspects without departing from the spirit or scope of the disclosure.

What is claimed is:

1. A processor-implemented method comprising:
   obtaining a plurality of optical sensor signal measurements of an optical sensor signal, the optical sensor signal measurements based, in part, on at least one cardiovascular parameter of a user;
   obtaining a plurality of motion sensor signal measurements of a motion sensor signal, the motion sensor signal measurements based, in part, on motion of the user;
   determining, based, in part, on a comparison of a spectral peaks obtained from the optical sensor signal measurements and spectral peaks obtained from the motion sensor signal measurements, a fundamental frequency associated with the optical sensor signal;

estimating a first heart rate based, in part, on the fundamental frequency; and obtaining a first quality metric associated with the first heart rate, the first quality metric being based, at least in part, on:

a first sum, wherein the first sum is obtained by adding an amplitude of a spectral peak corresponding to the fundamental frequency to amplitudes of spectral peaks in a first subset of spectral peaks in the optical sensor signal, wherein the first subset of spectral peaks is selected from spectral peaks associated with integral multiples of the fundamental frequency in the optical sensor signal, and a second sum obtained by adding the amplitudes of spectral peaks in a second subset of spectral peaks in the optical sensor signal, wherein the second subset of spectral peaks is selected from a set of spectral peaks in the optical sensor signal.

2. The processor-implemented method of claim 1, wherein:

the first quality metric is computed as a ratio of the first sum to the second sum.

3. The processor-implemented method of claim 1, further comprising:

obtaining a second quality metric associated with the first heart rate, the second quality metric based, in part, on:

a first power corresponding to a power of the spectral peak associated with the fundamental frequency, and a second power corresponding to a power at a predetermined spectral distance from the fundamental frequency.

4. The processor-implemented method of claim 3, wherein:

the second quality metric is obtained as a ratio of the first power to a sum obtained by adding the first power to the second power.

5. The processor-implemented method of claim 3, further comprising:

obtaining a third quality metric based, in part, on a mathematical combination of the first quality metric and the second quality metric.

6. The processor-implemented method of claim 5, further comprising:

estimating a second heart rate by performing adaptive smoothing of the first heart rate, wherein the adaptive smoothing is based, in part, on the third quality metric.

7. The processor-implemented method of claim 6, further comprising:

obtaining a fourth quality metric, wherein the fourth quality metric is dynamically obtained based, in part, on a comparison of the first heart rate and the second heart rate.

8. The processor-implemented method of claim 1, wherein determining the fundamental frequency comprises:

obtaining a frequency domain representation of the optical sensor signal from the plurality of optical sensor signal measurements and a frequency domain representation of the motion sensor signal from the plurality of motion sensor signal measurements;

comparing spectral peaks in the frequency domain representation of the optical sensor signal to spectral peaks in the frequency domain representation of the motion sensor signal to determine one or more non-motion related spectral peaks in the frequency domain representation of the optical sensor signal; and determining, from the one or more non-motion related spectral peaks in the frequency domain representation of the optical sensor signal, the fundamental frequency associated with the optical sensor signal.

9. A mobile device comprising:

an optical sensor to provide a plurality of optical sensor signal measurements of an optical sensor signal based, in part, on at least one cardiovascular parameter of a user;

a motion sensor to provide a plurality of motion sensor signal measurements of a motion sensor signal based, in part, on motion of the user;

a processor coupled to the optical sensor and the motion sensor, wherein the processor is configured to:

determine, based, in part, on a comparison of spectral peaks obtained from the optical sensor signal measurements and spectral peaks obtained from the motion sensor signal measurements, a fundamental frequency associated with the optical sensor signal;

estimate a first heart rate based, in part, on the fundamental frequency; and obtain a first quality metric associated with the first heart rate, the first quality metric being based, at least in part, on:

a first sum, wherein the first sum is obtained by adding an amplitude of a spectral peak corresponding to the fundamental frequency to amplitudes of spectral peaks in a first subset of spectral peaks in the optical sensor signal, wherein the first subset of spectral peaks is selected from spectral peaks associated with integral multiples of the fundamental frequency in the optical sensor signal, and a second sum obtained by adding the amplitudes of spectral peaks in a second subset of spectral peaks in the optical sensor signal, wherein the second subset of spectral peaks is selected from a set of spectral peaks in the optical sensor signal.

10. The mobile device of claim 9, wherein the processor is configured to:

obtain the first quality metric as a ratio of the first sum to the second sum.

11. The mobile device of claim 9, wherein the processor is further configured to:

obtain a second quality metric associated with the first heart rate, the second quality metric based, in part, on:

a first power corresponding to a power of the spectral peak associated with the fundamental frequency, and a second power corresponding to a power at a predetermined spectral distance from the fundamental frequency.

12. The mobile device of claim 11, wherein the processor is configured to:

obtain the second quality metric is obtained as a ratio of the first power to a sum obtained by adding the first power to the second power.

13. The mobile device of claim 11, wherein the processor is further configured to:

obtain a third quality metric based, in part, on a mathematical combination of the first quality metric and the second quality metric.

14. The mobile device of claim 13, wherein the processor is further configured to:

estimate a second heart rate by performing adaptive smoothing of the first heart rate, wherein the adaptive smoothing is based, in part, on the third quality metric.

15. The mobile device of claim 14, wherein the processor is further configured to:

obtain a fourth quality metric, wherein the fourth quality metric is dynamically obtained based, in part, on a comparison of the first heart rate and the second heart rate.

16. The mobile device of claim 9, wherein to determine the fundamental frequency, the processor is configured to:

obtain a frequency domain representation of the optical sensor signal from the plurality of optical sensor signal measurements and a frequency domain representation of the motion sensor signal measurements from the plurality of motion sensor signal measurements;

compare spectral peaks in the frequency domain representation of the optical sensor signal to spectral peaks in the frequency domain representation of the motion sensor signal to determine one or more non-motion related spectral peaks in the frequency domain representation of the optical sensor signal; and determine, from the one or more non-motion related spectral peaks in the frequency domain representation of the optical sensor signal, the fundamental frequency associated with the optical sensor signal.

17. An apparatus comprising:

optical sensing means to provide a plurality of optical sensing means signal measurements of an optical sensing means signal based, in part, on at least one cardiovascular parameter of a user;

motion sensing means to provide a plurality of motion sensing means signal measurements of a motion sensing means signal based, in part, on motion of the user;

processing means coupled to the optical sensing means and the motion sensing means, wherein the processing means comprises:

means for determining, based, in part, on a comparison of a spectral peaks obtained from the optical sensing means signal measurements and spectral peaks obtained from the motion sensing means signal measurements, a fundamental frequency associated with the optical sensing means signal;

means for estimating a first heart rate based, in part, on the fundamental frequency; and means for obtaining a first quality metric associated with the first heart rate, the first quality metric being based, at least in part, on:

a first sum, wherein the first sum is obtained by adding an amplitude of a spectral peak corresponding to the fundamental frequency to amplitudes of spectral peaks in a first subset of spectral peaks in the optical sensing means signal, wherein the first subset of spectral peaks is selected from spectral peaks associated with integral multiples of the fundamental frequency in the optical sensing means signal, and a second sum obtained by adding the amplitudes of spectral peaks in a second subset of spectral peaks in the optical sensing means signal, wherein the second subset of spectral peaks is selected from a set of spectral peaks in the optical sensing means signal.

18. The apparatus of claim 17, wherein the processing means further comprises:

means for obtaining a second quality metric associated with the first heart rate, the second quality metric based, in part, on:

a first power corresponding to a power of the spectral peak associated with the fundamental frequency, and a second power corresponding to a power at a predetermined spectral distance from the fundamental frequency.

19. The apparatus of claim 18, wherein the processing means further comprises:

means for obtaining a third quality metric based, in part, on a mathematical combination of the first quality metric and the second quality metric.

20. The apparatus of claim 19, wherein the processing means further comprises:

means for obtaining a second heart rate of the user by performing adaptive smoothing of the first heart rate, wherein the adaptive smoothing is based, in part, on the third quality metric.

21. The apparatus of claim 20, wherein the processing means further comprises:

means for dynamically obtaining a fourth quality metric based, in part, on a comparison of the first heart rate and the second heart rate.

22. The apparatus of claim 17, wherein means for determining the fundamental frequency comprises:

means for obtaining a frequency domain representation of the optical sensing means signal from the plurality of optical sensing means signal measurements and a frequency domain representation of the motion sensing means signal from the plurality of motion sensing means signal measurements;

means for comparing spectral peaks in the frequency domain representation of the optical sensing means signal to spectral peaks in the frequency domain representation of the motion sensing means signal to determine one or more non-motion related spectral peaks in the frequency domain representation of the optical sensing means signal; and means for determining, from the one or more non-motion related spectral peaks in the frequency domain representation of the optical sensing means signal, the fundamental frequency associated with the optical sensing means signal.

23. A non-transitory computer-readable medium embodying instructions, which, when executed by a processor, perform steps in a method comprising:

obtaining a plurality of optical sensor signal measurements of an optical sensor signal, the optical sensor signal measurements based, in part, on at least one cardiovascular parameter of a user;

obtaining a plurality of motion sensor signal measurements of a motion sensor signal, the motion sensor signal measurements based, in part, on motion of the user;

determining, based, in part, on a comparison of a spectral peaks obtained from the optical sensor signal measurements and spectral peaks obtained from the motion sensor signal measurements, a fundamental frequency associated with the optical sensor signal;

estimating a first heart rate based, in part, on the fundamental frequency; and obtaining a first quality metric associated with the first heart rate, the first quality metric being based, at least in part, on:

a first sum, wherein the first sum is obtained by adding an amplitude of a spectral peak corresponding to the fundamental frequency to amplitudes of spectral peaks in a first subset of spectral peaks in the optical sensor signal, wherein the first subset of spectral peaks is selected from spectral peaks associated with integral multiples of the fundamental frequency in the optical sensor signal, and a second sum obtained by adding the amplitudes of spectral peaks in a second subset of spectral peaks in the optical sensor signal, wherein the second subset of spectral peaks is selected from a set of spectral peaks in the optical sensor signal.

24. The non-transitory computer-readable medium of claim 23, wherein:
the first quality metric is computed as a ratio of the first sum to the second sum.

25. The non-transitory computer-readable medium of claim 23, further comprising:
obtaining a second quality metric associated with the first heart rate, the second quality metric based, in part, on:
a first power corresponding to a power of the spectral peak associated with the fundamental frequency, and
a second power corresponding to a power at a predetermined spectral distance from the fundamental frequency.

26. The non-transitory computer-readable medium of claim 25, wherein:
the second quality metric is obtained as a ratio of the first power to a sum obtained by adding the first power to the second power.

27. The non-transitory computer-readable medium of claim 25, further comprising:
obtaining a third quality metric based, in part, on a mathematical combination of the first quality metric and the second quality metric.

28. The non-transitory computer-readable medium of claim 27, further comprising:
obtaining a second heart rate of the user by performing adaptive smoothing of the first heart rate, wherein the adaptive smoothing is based, in part, on the third quality metric.

29. The non-transitory computer-readable medium of claim 28, further comprising:
obtaining a fourth quality metric, wherein the fourth quality metric is dynamically obtained based, in part, on a comparison of the first heart rate and the second heart rate.

30. The non-transitory computer-readable medium of claim 23, wherein determining the fundamental frequency comprises:
obtaining a frequency domain representation of the optical sensor signal from the plurality of optical sensor signal measurements and a frequency domain representation of the motion sensor signal measurements from the plurality of motion sensor signal measurements;
comparing spectral peaks the frequency domain representation of the optical sensor signal to spectral peaks in the frequency domain representation of the motion sensor signal to determine one or more non-motion related spectral peaks in the frequency domain representation of the optical sensor signal; and
determining, from the one or more non-motion related spectral peaks in the frequency domain representation of the optical sensor signal, the fundamental frequency associated with the optical sensor signal.

* * * * *